US012653241B2

(12) United States Patent
Chong et al.

(10) Patent No.: US 12,653,241 B2
(45) Date of Patent: *Jun. 16, 2026

(54) AEROSOL DEVICE AND METHOD FOR MOVING CONSUMABLE

(71) Applicant: CQENS Technologies Inc., Minneapolis, MN (US)

(72) Inventors: Alexander Chinhak Chong, St. Louis Park, MN (US); William Bartkowski, Edina, MN (US); David Crosby, Watsonville, CA (US); David Wayne, Aptos, CA (US); Gerard Shudall, Liverpool (GB)

(73) Assignee: COENS TECHNOLOGIES, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/362,115

(22) Filed: Oct. 17, 2025

(65) Prior Publication Data

US 2026/0041158 A1 Feb. 12, 2026

Related U.S. Application Data

(63) Continuation of application No. 19/102,289, filed as application No. PCT/US2022/039794 on Aug. 9, 2022, now Pat. No. 12,446,626.

(51) Int. Cl.
| | |
|---|---|
| *A24F 40/465* | (2020.01) |
| *A24F 40/20* | (2020.01) |
| *A24F 40/42* | (2020.01) |
| *A24F 40/70* | (2020.01) |
| *A61M 11/04* | (2006.01) |
| *A61M 15/00* | (2006.01) |

(Continued)

(52) U.S. Cl.
CPC ............ *A24F 40/465* (2020.01); *A24F 40/20* (2020.01); *A24F 40/42* (2020.01); *A24F 40/70* (2020.01); *A61M 11/042* (2014.02); *A61M 15/0021* (2014.02); *A61M 15/06* (2013.01); *H05B 6/108* (2013.01)

(58) Field of Classification Search
CPC ......... A24F 40/20; A24F 40/40; A24F 40/465
See application file for complete search history.

(56) References Cited

U.S. PATENT DOCUMENTS

| | | | |
|---|---|---|---|
| 2024/0114955 A1* | 4/2024 | Emmett et al. | ......... A24F 40/20 |
| 2025/0255348 A1 | 8/2025 | Chong et al. | |

* cited by examiner

*Primary Examiner* — Michael H. Wilson
*Assistant Examiner* — Ronnie Kirby Jordan
(74) *Attorney, Agent, or Firm* — Cisto & Thomas LLP

(57) ABSTRACT

A device for converting a consumable into an aerosol with high heat without burning the consumable using a moving aerosol-producing substrate to incrementally heat portions of the substrate to release the consumable from various portions of the substrate. The aerosol-producing substrate is placed in an aerosol-producing device in which a portion of the aerosol-producing substrate is surrounded by an induction heating element. The portion of the aerosol-producing substrate surrounded by the induction heating element can release consumable when the induction heating element is activated. A driver causes the aerosol-producing substrate to advance through the induction heating element causing another portion of the aerosol-producing substrate to enter the induction heating element, heating of which causes more release of the consumable.

14 Claims, 15 Drawing Sheets

(51) Int. Cl.
  *A61M 15/06*          (2006.01)
  *H05B 6/10*          (2006.01)

100

102

230

166

232

151

160

220

200

AEROSOL DEVICE AND METHOD FOR MOVING CONSUMABLE

CROSS-REFERENCE TO RELATED APPLICATION

This patent application is a continuation application of U.S. patent application Ser. No. 19/102,289 filed Feb. 7, 2025, which is a national phase application of United States PCT/US2022/039794, entitled "Aerosol Device and Method for Moving Consumable," filed Aug. 9, 2022, which applications are incorporated in their entirety here by this reference.

TECHNICAL FIELD

This invention relates to devices for aerosolizing medicants via a high-temperature, non-combusting inductive heating method, and uses thereof. The invention further relates to methods and devices for producing an aerosol from tobacco and/or other non-medicant substances using similar methods and devices.

BACKGROUND

When faced with a condition giving rise to bodily discomfort, such as a diseased state, disorder, ailment, normal bodily disruptions, and the like, most people turn to medicants, such as drugs, supplements, herbs, and the like for immediate relief from the symptoms that arise from the underlying condition. There are certain legal and widely available over-the-counter (OTC) medications and supplements that have beneficial effects when used for a variety of common conditions. There are also certain controlled narcotics and pharmaceuticals prescribed by doctors for a variety of more serious conditions.

One of the most common routes of administration of these OTC and prescription drugs is oral administration. As with any oral delivery of medication, however, it must pass through the digestive tract. There are a number of disadvantages of oral administration. For example, because the drug has to pass through the digestive system, the onset of activation of the drug is slow. In addition, in the digestive tract the drug may be inactivated or destroyed, and therefore, lose its potency or efficacy. The drug itself can also cause problems in the digestive tract, or side effects, such as loss of appetite, diarrhea, acidity, and the like. Furthermore, patients may be reluctant or unable to swallow oral medication in the form of a pill.

Certain medicants are intended to affect the brain or the brain's actions or activities but, given the accepted method of ingestion—gastrointestinal, intravenous, or intramuscular—these medicants can also have a variety of discomforting side effects due to the nature of ingestion or injection. These include, but are not limited to gastro-intestinal complications, digestive disorders, high blood pressure, and/or headaches, as well as the reluctance of users to self-administer medicants by injection.

Other routes of delivery exist, such as intradermal injections, patch applications, inhalations, and the like. Each of these has its own advantages and disadvantages. Therefore, there is still room for improving routes of administration of medicants.

For example, there are varieties of medicants that are safer, more effective, and more efficient with respect to both safety and efficacy if their ingestion is via inhalation of an aerosol, such as a gas, vapor, mist, and any other inhalant, containing the medicant or its active ingredient rather than by gastrointestinal, intravenous or intramuscular delivery.

Additionally, certain methods to aerosolize and deliver these medicants have drawbacks as well, specifically those that aerosolize the medicant itself, changing the molecular or chemical structure of the medicant or those that might aerosolize at a high temperature—extending the duration heating and raising the risk of changing the molecular or chemical structure of the active ingredient. Other drawbacks of current aerosolization techniques include the transport, storage and merchandising of certain of these medicants in cartridges that are prone to leaking and, in many cases, are designed and constructed with cartridge materials that are not environmentally friendly, containing plastics and other materials that are not biodegradable.

In order to ensure that the medicant is delivered intact via the high temperature, non-combusting inductive method, it is preferred that the method of aerosolization does not change the chemical or fundamental molecular structure of the medicant or other materials that make up the medicant, or if such changes occur, that they will not interfere with, and/or improve, the efficacy of the medicant.

Therefore, there is still a need for improving the routes of administration of medicants. In particular, there is still a need for improving methods of aerosolizing medicants for inhalation that would also provide the added benefit of metering, monitoring and measuring inhalers exact dosages without destroying the active ingredient or adding other chemicals to the aerosol as a result of energy inefficiency or prolonged heating duration. There is also the need for consumable embodiments that are biodegradable and do not contain materials that are not consistent with environmentally friendly disposal.

In addition to medicant delivery systems, heat-not-burn (HNB) devices are a type of device generally used to heat tobacco at temperatures lower than those that cause combustion to create an aerosol containing nicotine and other tobacco constituents, which is then made available to the device's user. In some embodiments, the heated element or susceptor is placed inside a solid tobacco product with a coil wrapped around the tobacco product and susceptor to cause the susceptor to heat through an inductive mechanism. Unlike traditional cigarettes, the goal is not to burn the tobacco, but rather to heat the tobacco sufficiently to release the nicotine and other constituents through the production of aerosol. Igniting and burning the cigarette creates unwanted toxins that can be avoided using the HNB device. There is a fine balance, however, between providing sufficient heat to effectively release the tobacco constituents in aerosol form and not burn or ignite the tobacco. Current HNB devices on the market have not found that balance, either heating the tobacco at temperatures that produce an inadequate amount of aerosol or over heating the tobacco and producing an unpleasant or "burnt" flavor profile. Additionally, the current methodology leaves traditional HNB device internal components dirtied with burning tobacco byproducts and the byproducts of accidental combustion.

Furthermore, in order to ensure the state change from a solid or liquid state to an aerosol state in a rapid, energy efficient manner via high temperature, non-combusting inductive heating, the formulation must be configured in a way that eliminates air flow between the formulation and the inductive system's susceptor.

For the foregoing reasons there is a need for a device, which will affect the temperature at which the tobacco will be heated via the inductive method to reduce the risk of combustion-even at what would otherwise be sufficient temperatures to ignite—while increasing the efficiency and flavor profile of the aerosol produced. There is also a need for a device that uses a unique consumable that is inexpensive to produce and when used in an associated device, provides a satisfying user experience by moving the consumable past an inductive coil for successive inhalations.

SUMMARY

The present invention is directed towards devices and methods for delivering a consumable in an aerosolized state for inhaled administration and ingestion using a high temperature, non-combusting inductive method to aerosolize an embodiment of the formulation's design and configuration.

In particular, the present invention is directed towards further improvements in heat-not-burn devices, such as those described in U.S. Pat. No. 10,750,787; PCT/US2019/012204; and PCT/US2020/040779. In general, the heat-not-burn device is a device for converting a consumable into an aerosol that contains certain of its constituents but limiting the byproducts most often associated with combustion, for example, smoke, ash, tar and certain other potentially harmful chemicals. It does so by using high heat without burning the consumable by packaging the consumable containing an internal susceptor inside an encasement. This invention can involve positioning and incrementally advancing heat along a consumable tobacco component with the use of an induction heating element wrapped around the consumable-containing package to heat the susceptor using a magnetic field generated by the induction heating element, by moving either the heating element, the consumable, or both.

Another object of the present invention is a consumable tobacco component comprised of at least one encasement containing a consumable tobacco preparation- and an induction heating source. The encasement may be a paper, fabric, plastic, or woven sheet or any other material that is porous enough to convey an aerosol generated during heating of the consumable. The consumable may be assembled with two sheets of this material, a top and a bottom, sandwiching the susceptor within the consumable preparation, and then the two sheets may be folded together to enclose the consumable preparation. Several of these "packets" may be used in a single consumable, or just one packet.

In alternative embodiments, the encasement may be an aluminum shell with pre-set openings. The encasements may be coated with a gel that seals the openings until an inductive heating process melts the gel, clearing the openings. In some embodiments, the gel can include a flavoring agent that can add flavor to or enhance the flavor of the tobacco aerosol.

In some embodiments, multiple encasements may be stacked inside a paper tube with spaces between them, formed by excess wrapping at the bottom end of each encasement and channels on either side to allow for the aerosol produced to pass through. When the inductive heating source is activated, the pre-set openings are cleared, and flavor is combined with the aerosol to travel through the tube and be made available to the user of the device.

Using these methods and apparatus, the device is required to heat less mass, can heat-up immediately, cool down quickly and conserve power, allowing for greater use between re-charging sessions. This contrasts with the well-known, current, commercially available heat-not-burn devices.

Another object of the present invention is to create a consumable-containing package that is easy to replace and minimizes fouling the inside of the case during use so as to reduce cleaning efforts of the case.

Another object of the present invention is to move the susceptor or the consumable relative to the heating element to heat segments of the consumable independent of other segments. "Segments" in this context refers to either physically segmented consumable materials, or contiguous consumable materials that are sequentially heated as they move past the inductive coil or vice versa.

Another object of the invention is to aerosolize the consumable, which can be compressed around a susceptor in such a way as to eliminate any flow of air between the consumable and the susceptor. For example, the aerosol-producing substrate can contain inert non-reactive compounds that are mixed with a form of the consumable and then tightly compressed around a susceptor. The formulation can be aerosolized using a hand-held high temperature inductive heating device configured to the embodiment of the consumable.

Accordingly, the device, method, and formulation of the present invention can be used to aerosolize a variety of consumables, preferably, medicants. For example, these medicants include, but are not limited to those configured to increase bronchial efficiency, support tobacco and nicotine cessation, assist in relaxation, ease anxiety, discourage disruptive ideation, manage pain, increase concentration, aid in restful sleep, aid in sexual activity, increase energy and wakefulness and counteract the harmful effects of the overdosing of certain other medicants. In addition, these consumables may include tobacco, cannabis, or other substances that can be ingested via inhalation by consumers.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Heat-Not-Burn Device

The invention of the present application is a device for generating aerosols from a consumable-containing product for inhalation in a manner that utilizes relatively high heat with minimal burning of the consumable-containing product. For the purposes of this application, the term "consumable" is to be interpreted broadly to encompass any type of pharmaceutical agent, drug, chemical compound, active agent, constituent, any other medicant, and the like, regardless of whether the consumable is used to treat a condition or disease, is for nutrition, is a supplement, or used for recreation. By way of example only, a consumable can include pharmaceuticals, nutritional supplements, and over-the-counter medicants, such as but not limited to, tobacco, cannabis, hemp, lavender, kava, coffee, caffeine, lobelia, hoodia, melatonin, epimedium, guarana, ginseng and the like.

Figure 1:
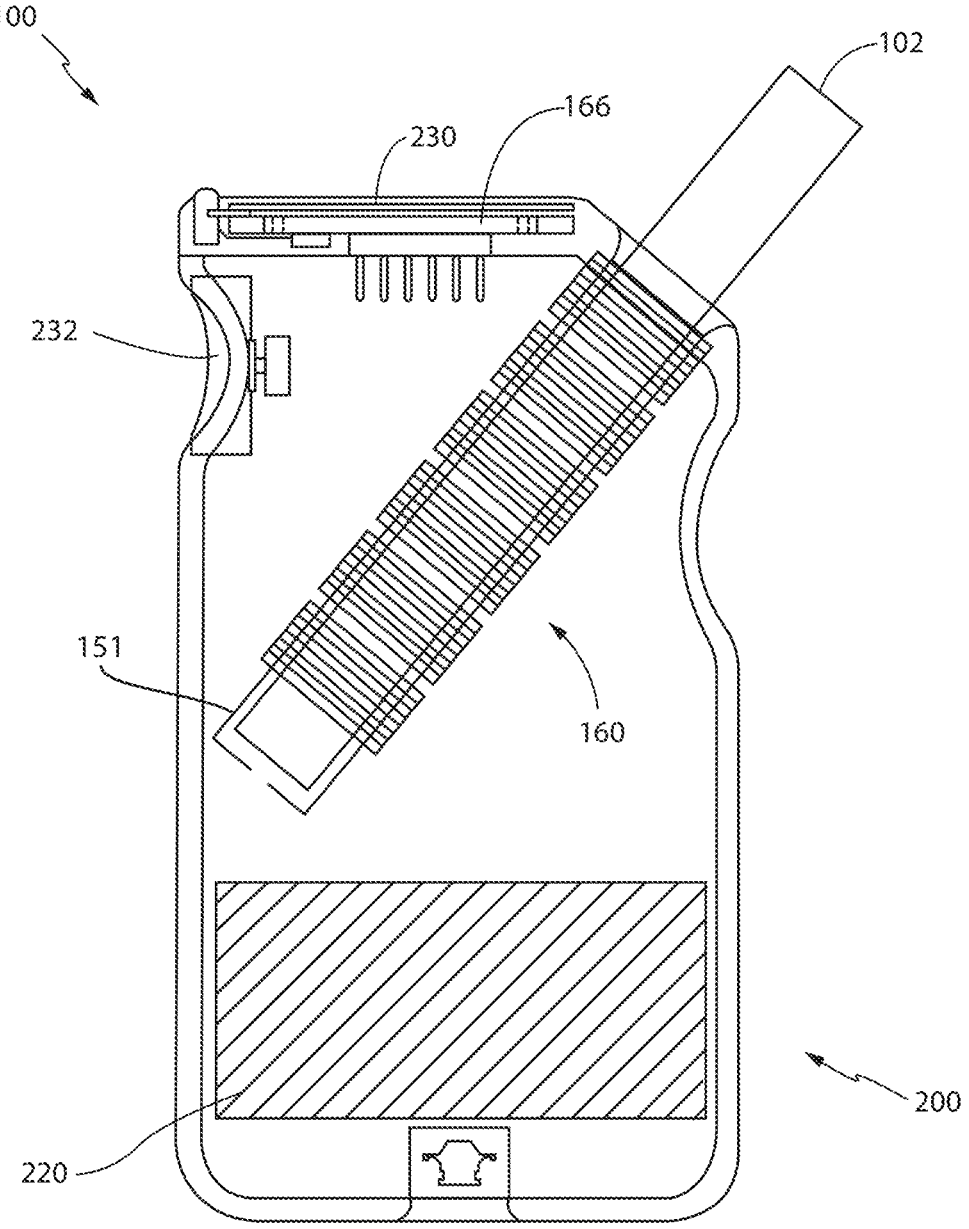
FIG. 1 shows a side view inside of an embodiment of the present invention assembled in a HNB device.
Figure 2A:
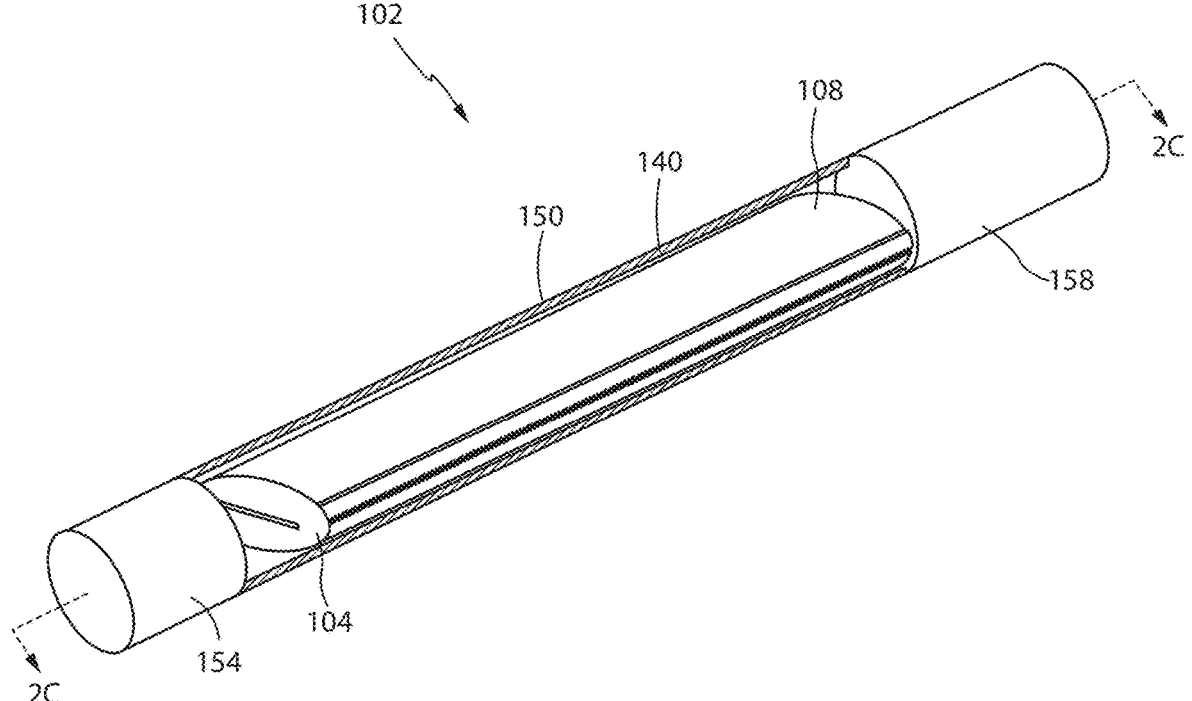
FIG. 2A shows a perspective view of an embodiment of the present invention assembled into a consumable-containing package.
Figure 2B:
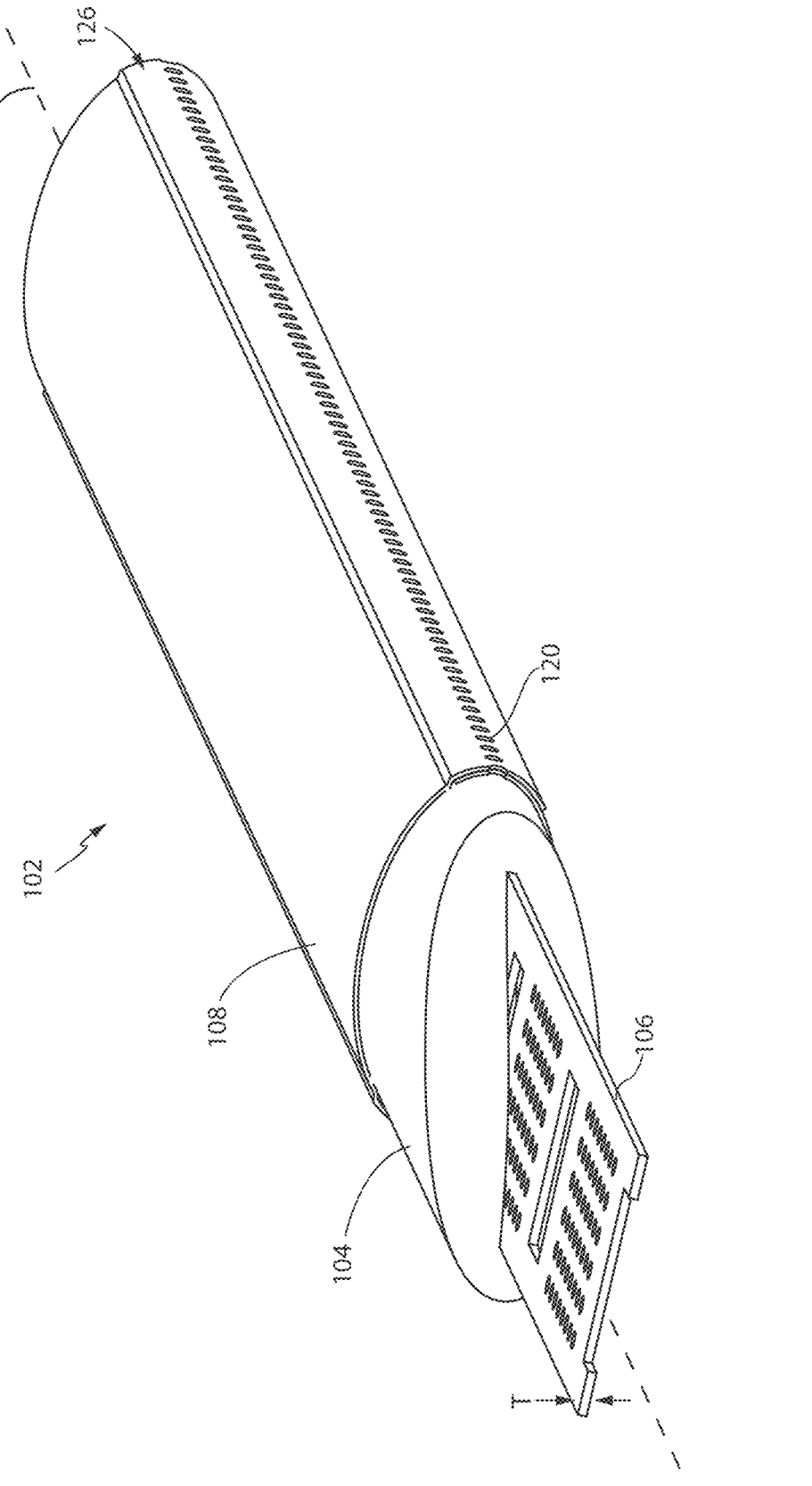
FIG. 2B shows a perspective view of the embodiment shown in FIG. 2A with portions of the consumable-containing package cut away and/or removed to reveal the susceptor.
Figure 2C:
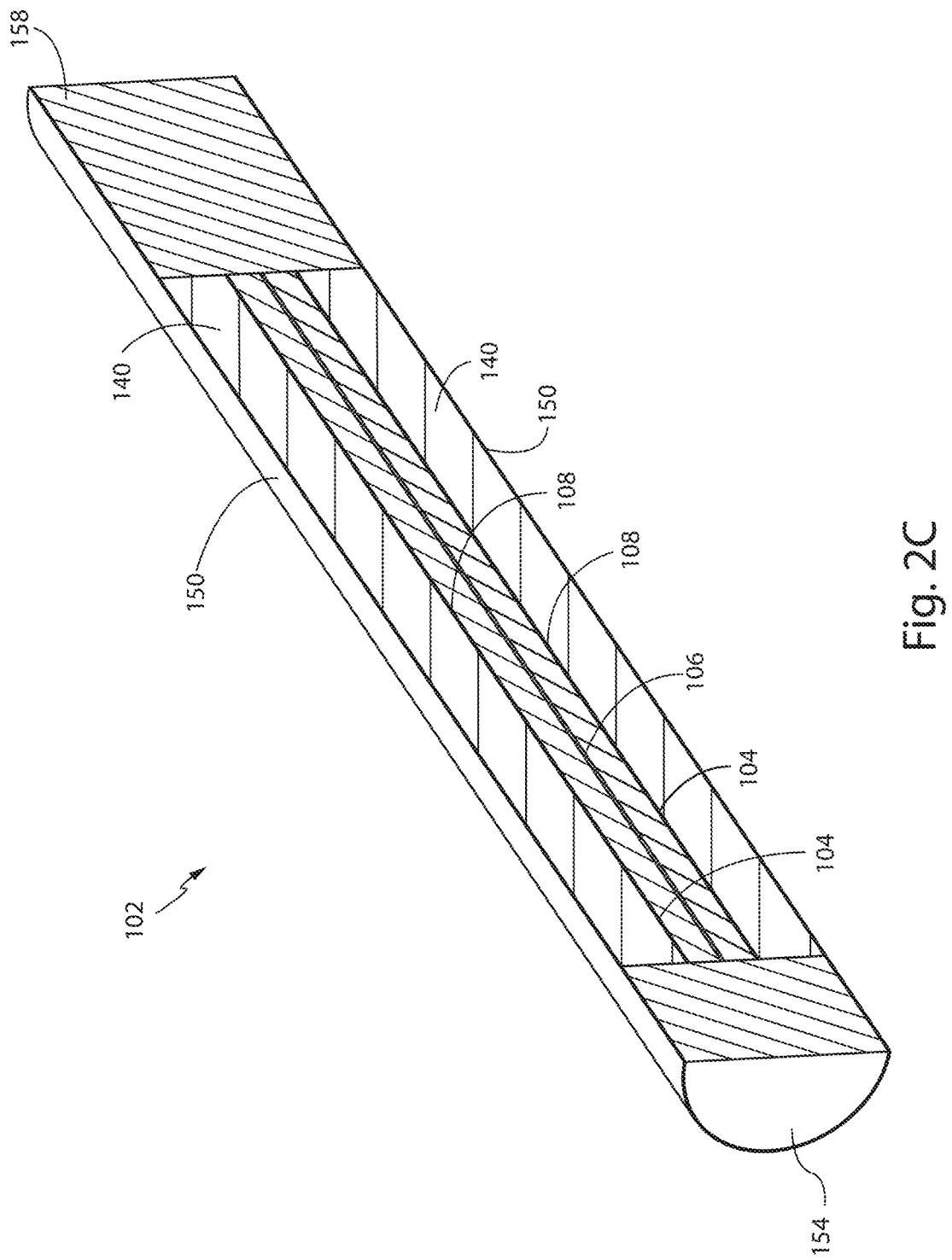
FIG. 2C shows a cross-sectional view of the embodiment shown in FIG. 2A cut along line 2C-2C.
Figure 2D:
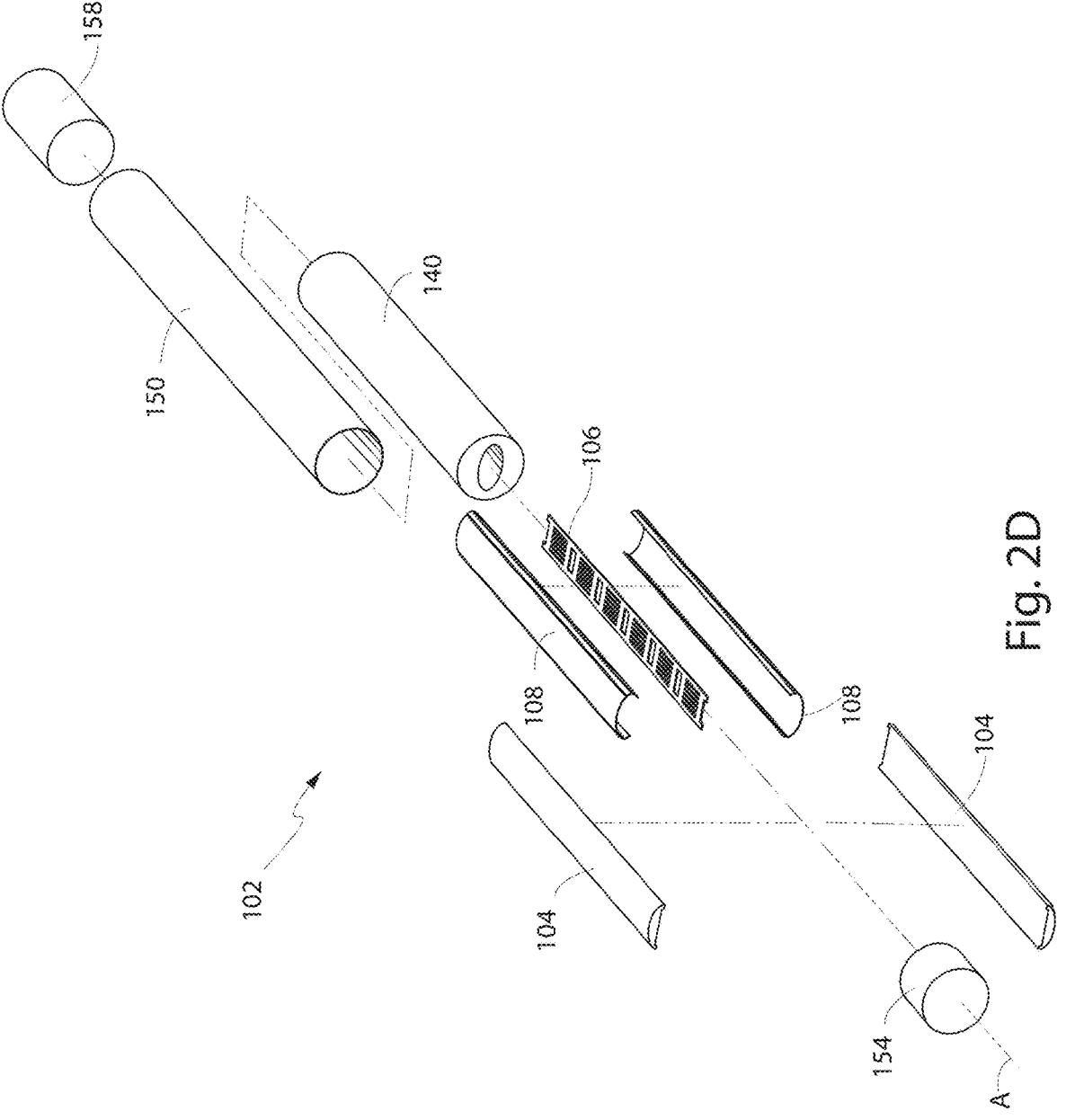
FIG. 2D shows an exploded view of the consumable-containing package shown in FIG. 2A.
Figure 2E:
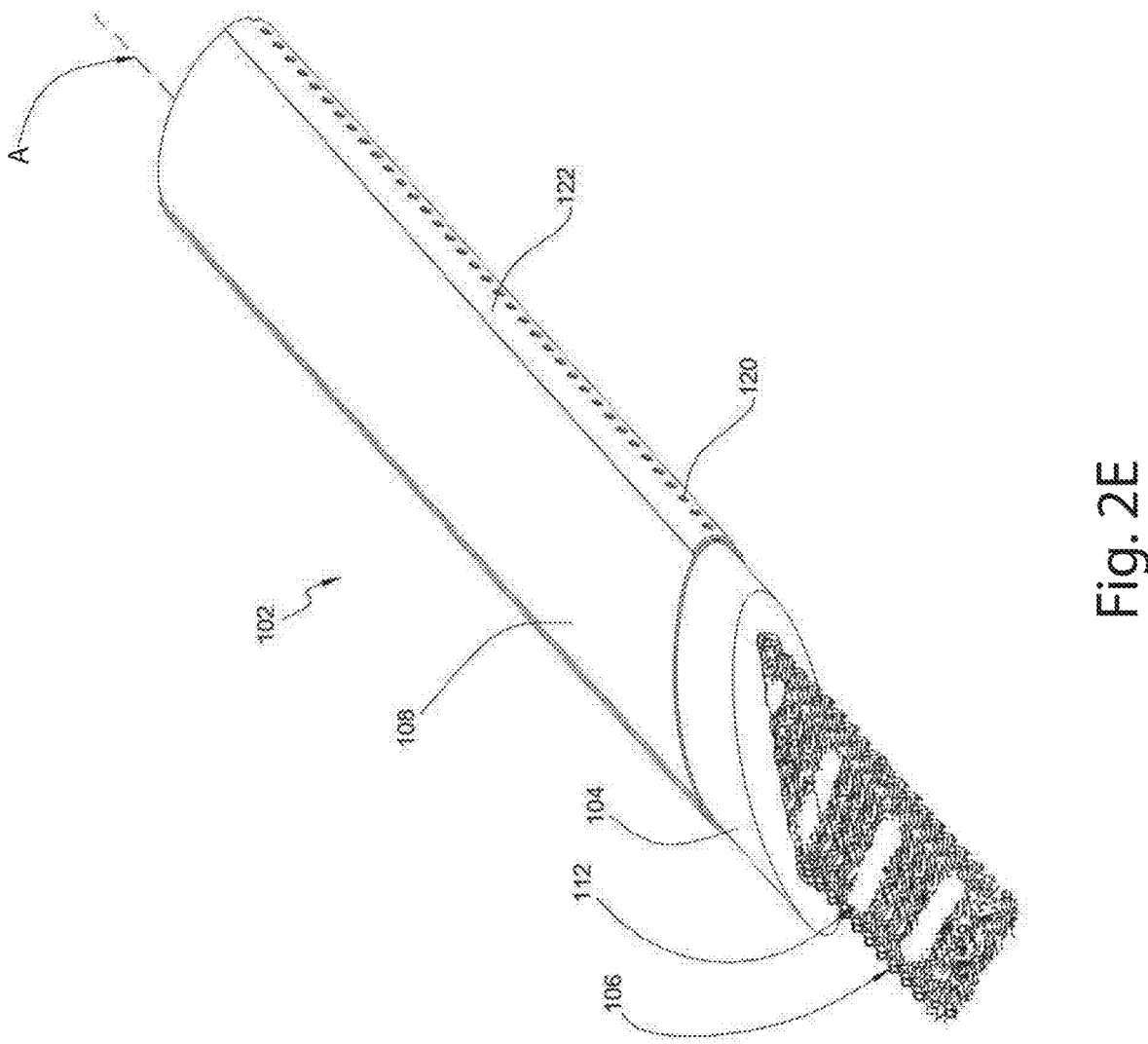
FIG. 2E shows a perspective view of the consumable-containing package with another embodiment of the susceptor with portions of the consumable-containing package cut away and/or removed to reveal the susceptor.

An example of an HNB device 100 is shown in FIGS. 1-2E, and described fully in U.S. Pat. No. 10,750,787; PCT/US2019/012204; and PCT/US2020/040779, which applications are incorporated in their entirety here by this reference. The device 100 comprises a consumable-containing package 102 and an aerosol-producing device 200. The consumable-containing package 102 comprises an aerosol-producing substrate 104 that releases an active agent (the consumable) when heated, and a susceptor 106 embedded therein to heat the aerosol-producing substrate 104. The device 100 generates aerosols through a heat-not-burn process in which an aerosol-producing substrate 104 is exposed to an aerosolizing thermal state, such as high aerosolizing temperatures and the absence of oxygen, which does not burn an aerosol-producing substrate 104 within the consumable-containing package 102, but does release the active ingredient (the consumable) from the aerosol-producing substrate 104 in the form of an aerosol product that can be inhaled. Thus, an aerosol-producing substrate 104 is any product that contains an active ingredient that can be released into aerosol form when heated to the proper temperature and condition. Any description of the invention to a specific application, such as to a tobacco product, is provided only as a concrete example, and is not intended to be limiting. As such, the invention is not limited to use with tobacco products only.

With reference to FIG. 1, the aerosol-producing device 200 comprises a receiver 151 to contain a consumable-containing package 102, an induction heating element 160 to heat the susceptor 106, a system controller 166 to control the induction heating element 160, and a power source 220 to power the device 100. A user interface 230 operatively connected to the controller 166 can be provided to facilitate ease of operation. A trigger 232 can be provided to actuate the device 100, or the device 100 can be activated through the user interface 230.

With reference to FIGS. 2A-2E, the consumable-containing package 102 is the component that is heated to release the consumable (i.e. active agent) in aerosol form. The consumable-containing package 102 comprises an aerosol-producing substrate 104, and the susceptor 106 surrounded by the aerosol-producing substrate 104 for heating the aerosol-producing substrate 104 from the inside out through an inductive heating system. In some embodiments, the consumable-containing package 102 can have an encasement 108 to at least partially contain the aerosol-producing substrate 104 and the susceptor 106. For example, the aerosol-producing substrate 104 can be completely covered by the encasement 108. In some embodiments, the aerosol-producing substrate 104 can be partially covered by the encasement 108 such that portions of the aerosol-producing substrate 104 is exposed, such as all or portions of the ends, the top, the bottom, or any other portion of the aerosol-producing substrate 104. In some embodiments, the consumable-containing package 102 can further comprise a housing 150 to hold one or more aerosol-producing substrates 104 with embedded susceptors 106 with or without the encasement 108.

The Susceptor

The susceptor 106 is the component that is heated through the inductive method and heats the aerosol-producing substrate 104 from the inside out. As such, the susceptor 106 is made of a metal that can be heated through an inductive method, such as ferrous metals. Other metals or materials that have the capacity to inductively heat the aerosol-producing substrate 104 may also be used. To maximize efficient heating of the aerosol-producing substrate 104, the susceptor 106 generally matches the shape of the largest cross-sectional area of the aerosol-producing substrate 104 so as to maximize the surface area with which the aerosol-producing substrate 104 comes into contact with the susceptor 106, but other configurations may also be used.

The susceptor 106 can be machine extruded, made of metal particles that are sintered or otherwise fused, metal wool, stamped, pressed, or any other number of methods that can produce a satisfactory susceptor. Some of these methods are described in U.S. Pat. No. 10,750,787; PCT/US2019/012204; PCT/US2020/040779, and U.S. application Ser. No. 17/687,470, which are all incorporated here in their entirety by this reference. In some embodiments, an aerosol-producing substrate 104 can be combined with or incorporated into a susceptor 106 by co-extruding it with the susceptor 106 to create a layer of the aerosol-producing substrate 104 on top or on bottom of the layer of the susceptor 106. In some embodiments, two layers of the aerosol-producing substrate 104a, 104b can be co-extruded with the susceptor 106 in between to create a sandwich around the susceptor 106 that can be compressed in between the two layers of the aerosol-producing substrate 104*a*, 104*b*. The co-extruded material can then be cut to the appropriate size.

In some embodiments, in which the susceptor 106 is steel wool or metal particles, the consumable can be incorporated directly into the susceptor 106, for example, in a fluid (e.g., liquid, semi-liquid, viscous substance, and the like) or loose solid (e.g., powder, grains, granules, and the like) form, in which case the susceptor 106 has the dual function of being the heating element and the aerosol-producing substrate 104. As such, the aerosol-producing substrate 104 can be the susceptor 106 combined with the consumable incorporated therein.

The Aerosol-Producing Substrate

The design of the aerosol-producing substrate 104 is to minimize the amount of air to which the aerosol-producing substrate 104 is exposed. This eliminates or mitigates the risk of oxidation or combustion during storage or during the heating process. As a result, at certain settings, it is possible to heat the aerosol-producing substrate 104 to temperatures that would otherwise cause combustion when used with prior art devices that allow more air exposure.

As such, in some embodiments, the aerosol-producing substrate 104 is made from a powdered form of the consumable that is compressed into a hard, compressed pellet, rod, or cuboid. Compression of the consumable reduces the oxygen trapped inside the aerosol-producing substrate 104, and limits migration of oxygen into the aerosol-producing substrate 104 during storage and heating.

In some embodiments, the aerosol-producing substrate 104 may be one elongated unit defining a longitudinal axis A in the form of a rod or stick as shown in FIGS. 2A-2E. The aerosol-producing substrate 104 may be an elongated cylinder or tube having a circular transverse cross-section, an oval transverse cross-section, a rectangular transverse cross-section, a polygonal transverse cross-section, and the like. In some embodiments, the aerosol-producing substrate 104 may be a plurality of cylindrical tablets or pellets stacked on top of one another.

In a preferred embodiment, the aerosol-producing substrate 104 may be a slightly elongated cuboid in shape defining a longitudinal axis A, as shown in FIGS. 3A-3C and 4A-4B. Other cuboid shapes may also be used as well as a combination of generally planar and/or rounded faces in a generally cuboid shape.

The susceptor 106 may be similarly elongated and embedded in the aerosol-producing substrate 104, preferably, along the longitudinal axis A and extending substantially the length L of the aerosol-producing substrate 104. The susceptor 106 may also extend substantially the width W of the aerosol-producing substrate 104. In other embodiments, the susceptor 106 may extend beyond the width (or diameter) and length of the aerosol-producing substrate 104, or be substantially shorter than either dimension.

In some embodiments, the aerosol-producing substrate 104 can take on any other shape, including spherical, ovoid, elliptical, and even amorphous. In general, the susceptor 106 can pattern the shape of the aerosol-producing substrate 104 to maximize the surface area contact between the susceptor 106 and the aerosol-producing substrate 104; however, the susceptor 106 can be other shapes as well, including a plurality of susceptors 106 being sporadically distributed within the aerosol-producing substrate 104.

In yet another alternative embodiment, the aerosol-producing substrate 104 could be formed into tiny pellets, grains, powder, or other form that can be encapsulated to further reduce the air available to the consumable.

In some embodiments, the aerosol-producing substrate 104 can comprise a ground up source of the consumable made into powder form, then combined with a susceptor 106 by compressing tightly around the susceptor 106. By way of example only, the source of the consumable may be a plant, seed, flower, root, leaf, plant component, or any other source from which the consumable can be extracted. These components can be dried, ground up, and mixed with other components known for creating pellets and tablets to compress around a susceptor 106 to form the pellet, tablet, or rod around the susceptor 106. The compressed pellet, tablet, or rod can be encased inside the encasement 108 to form the consumable-containing package 102.

The Encasement

The invention of the present application is directed towards the construction of the consumable-containing package 102, and a structure that moves the consumable-containing package 102 past an inductive coil 160 to heat segments of the consumable-containing package 102 in a sequential manner.

In some embodiments as best seen in FIGS. 2A-2E, an encasement 108 contains the aerosol-producing substrate 104 with the susceptor 106 embedded therein. In some embodiments, the encasement 108 may be configured with holes 120 to allow the aerosol to escape from the encasement 108, or the encasement 108 may be a permeable membrane, paper, fabric, or other material to allow the aerosol to escape. The aerosol-producing substrate 104 can be placed inside a housing 150 that can mimic a cigarette. In some embodiments, a filter 140 can surround the encasement 108. The housing 150 may be capped with an end cap 154 at one end 152 and a mouthpiece 158 at the opposite end 156. The end cap 154 may be comprised of a type of filter material. The mouthpiece 158 allows the user to draw the heated consumable aerosol out of the aerosol-producing substrate 104 along the housing 150 towards the mouthpiece 158 and into the user's mouth. As such, the mouthpiece 158 may also comprise a type of filter, similar to that of the end cap 154. Adjacent to the mouthpiece 158 may be a plurality of holes 446 through which air can be drawn into when the user takes a drag on the housing 150 by sucking on the mouthpiece 158.

In a preferred embodiment, the encasement 108 comprises a top sheet 108*a* and a bottom sheet 108*b*, which may be two separate sheets or one contiguous sheet. The sheets 108*a*, 108*b* may comprise a permeable material that allows aerosol to escape, which may be filter paper, porous paper, fabric, plastic, membrane, metal with holes, tea bag material, or cigarette filter media (cellulose), or any suitable material.

The permeable nature of the encasement 108 can expose the aerosol-producing substrate 104 to air and potential oxidation/degradation. To prevent this, the pores or openings in the encasement 108 may be temporarily sealed using a coating. The coating is preferably made of a composition that melts and/or becomes permeable at temperatures that create consumable aerosols. Therefore, as the susceptor 106 is heated, due to the lack of air inside the encasement 108, the aerosol-producing substrate 104 can be raised to exceedingly high temperatures without combusting. As the susceptor 106 reaches high temperatures, the consumable aerosols that begin to form, are not able to escape. When the coating melts or becomes permeable, the consumable aerosols are able to escape the encasement 108 for inhalation. In the preferred embodiment, the coating may be propylene glycol alginate ("PGA") gel or a food grade starch. The coating may also include a flavoring. Therefore, as the coating melts away and the consumable aerosol is released, the flavoring is also released with the consumable aerosol. In some embodiments, the flavoring can be mixed with additives.

Figure 3A:
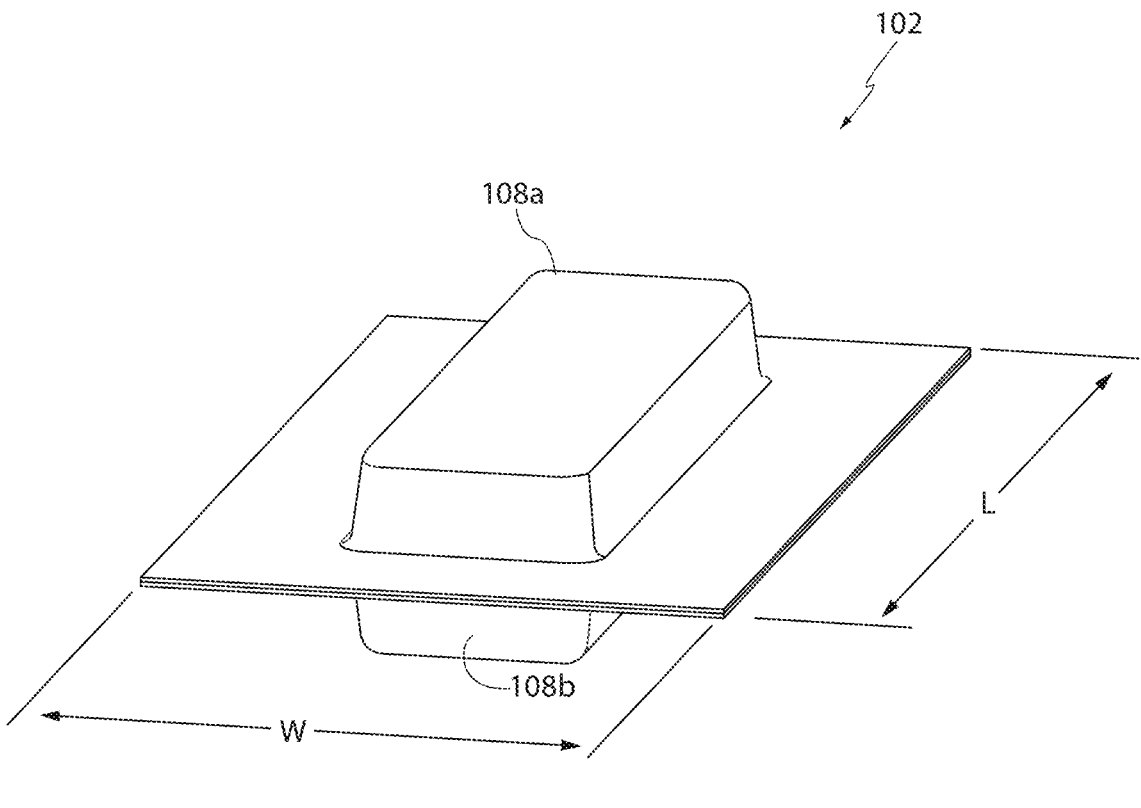
FIG. 3A shows a perspective view of an embodiment of a consumable-containing package.
Figure 3B:
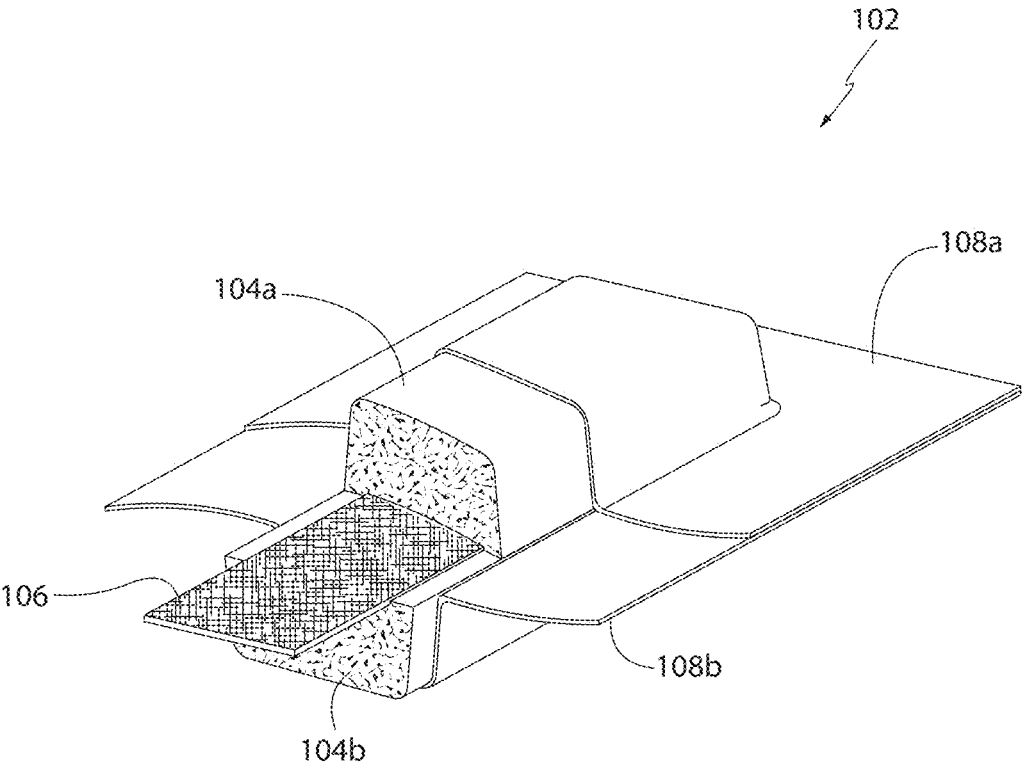
FIG. 3B shows a perspective view of the embodiment shown in FIG. 3A with portion of the consumable-containing package and consumable removed to show the interior configuration.
Figure 3C:
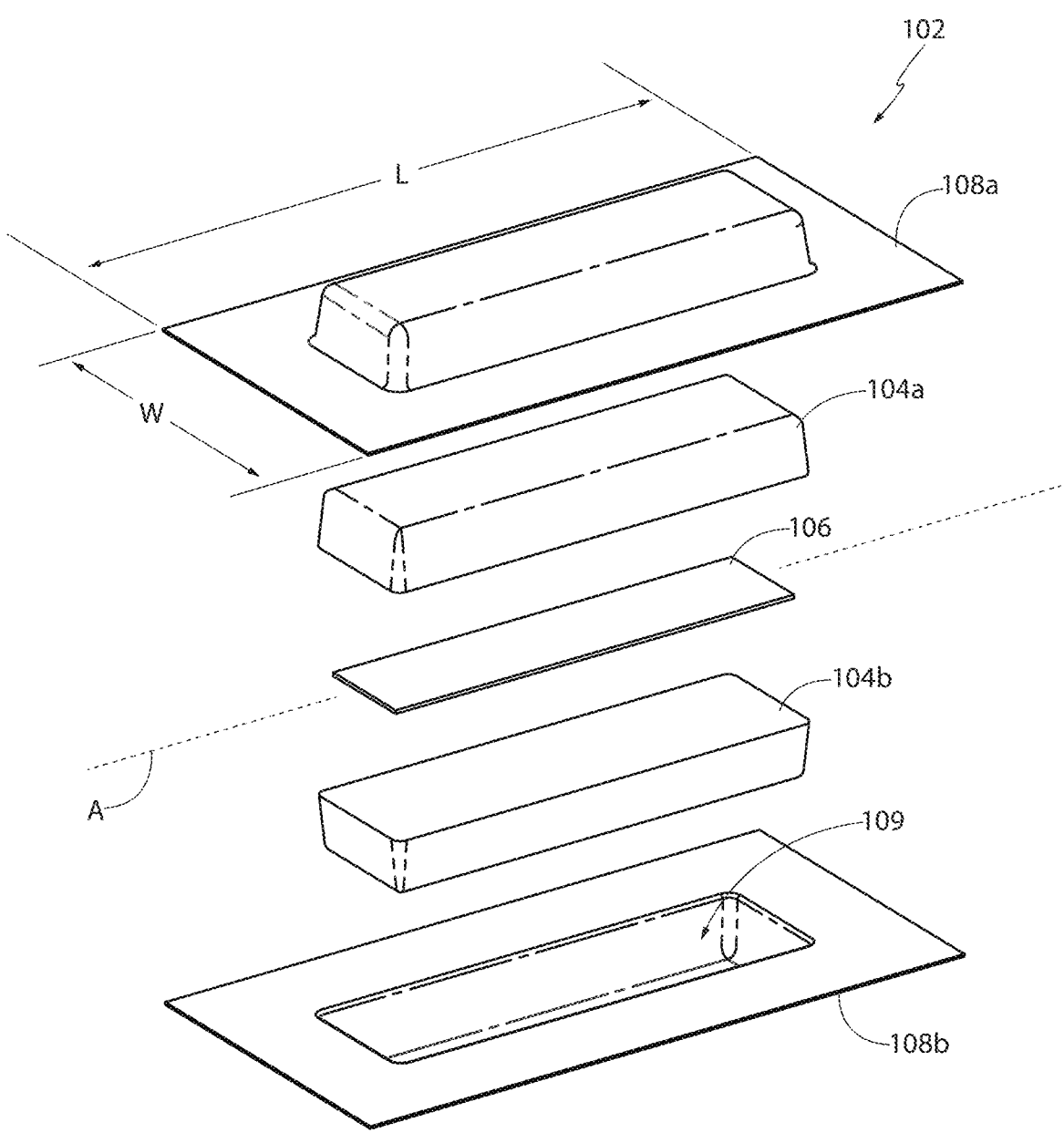
FIG. 3C shows an exploded view of the embodiment shown in FIG. 3A.

In a preferred embodiment, the encasement 108 may comprise a top portion 108a and a bottom portion 108b, which portions may be separate pieces or one contiguous piece. Preferably, the top and bottom portions of the encasement 108a, 108b have pre-formed cup-like indentations or cavities 109 to surround the aerosol-producing substrate 104, as shown in FIG. 3C. Alternatively, one or both of the top and bottom portions of the encasement 108a, 108b may be flat and then pressed or stretched around the aerosol-producing substrate 104 during production.

Figure 4A:
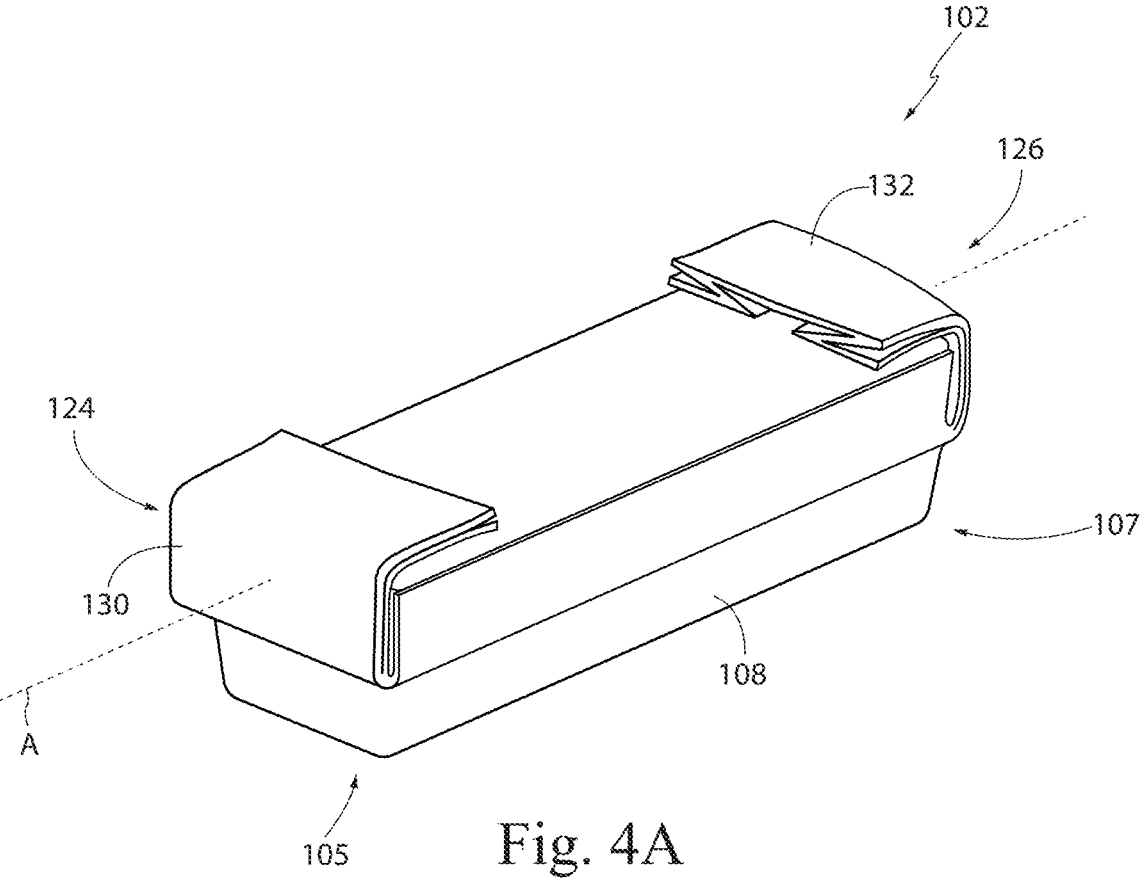
FIG. 4A shows a perspective view of another embodiment of the present invention.
Figure 4B:
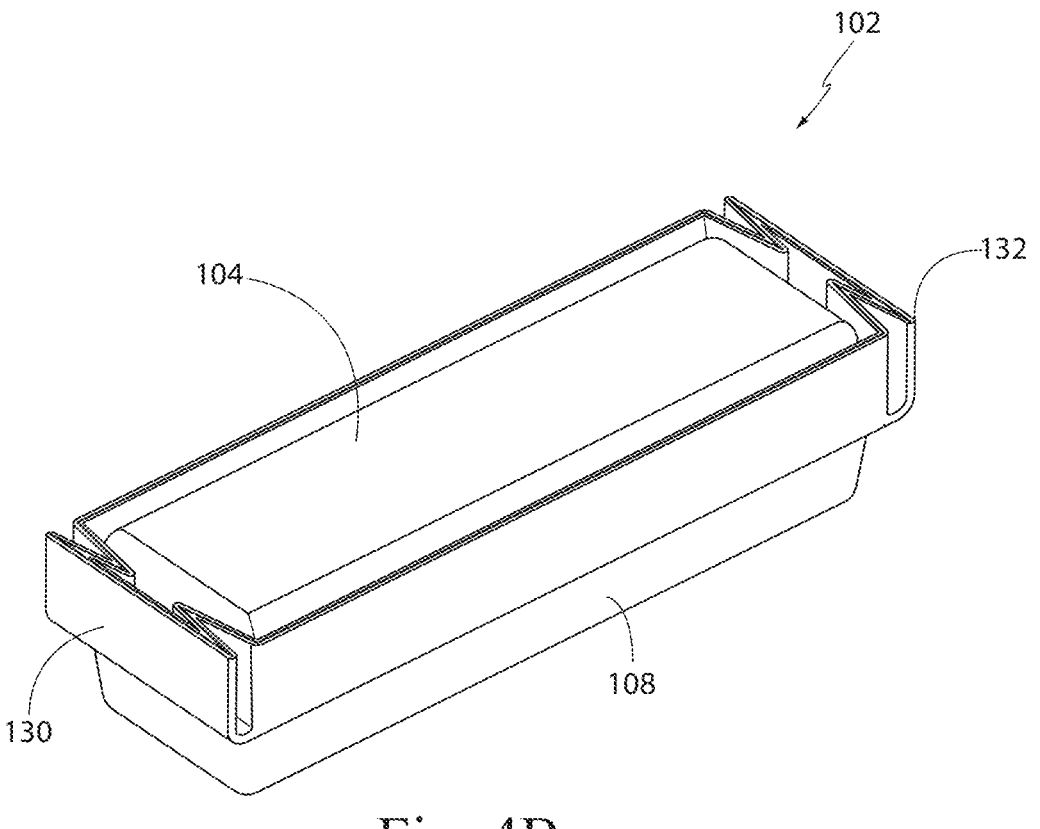
FIG. 4B shows the embodiment in FIG. 4A in an open configuration.
Figures 5A, 5B, 5C, 5D:
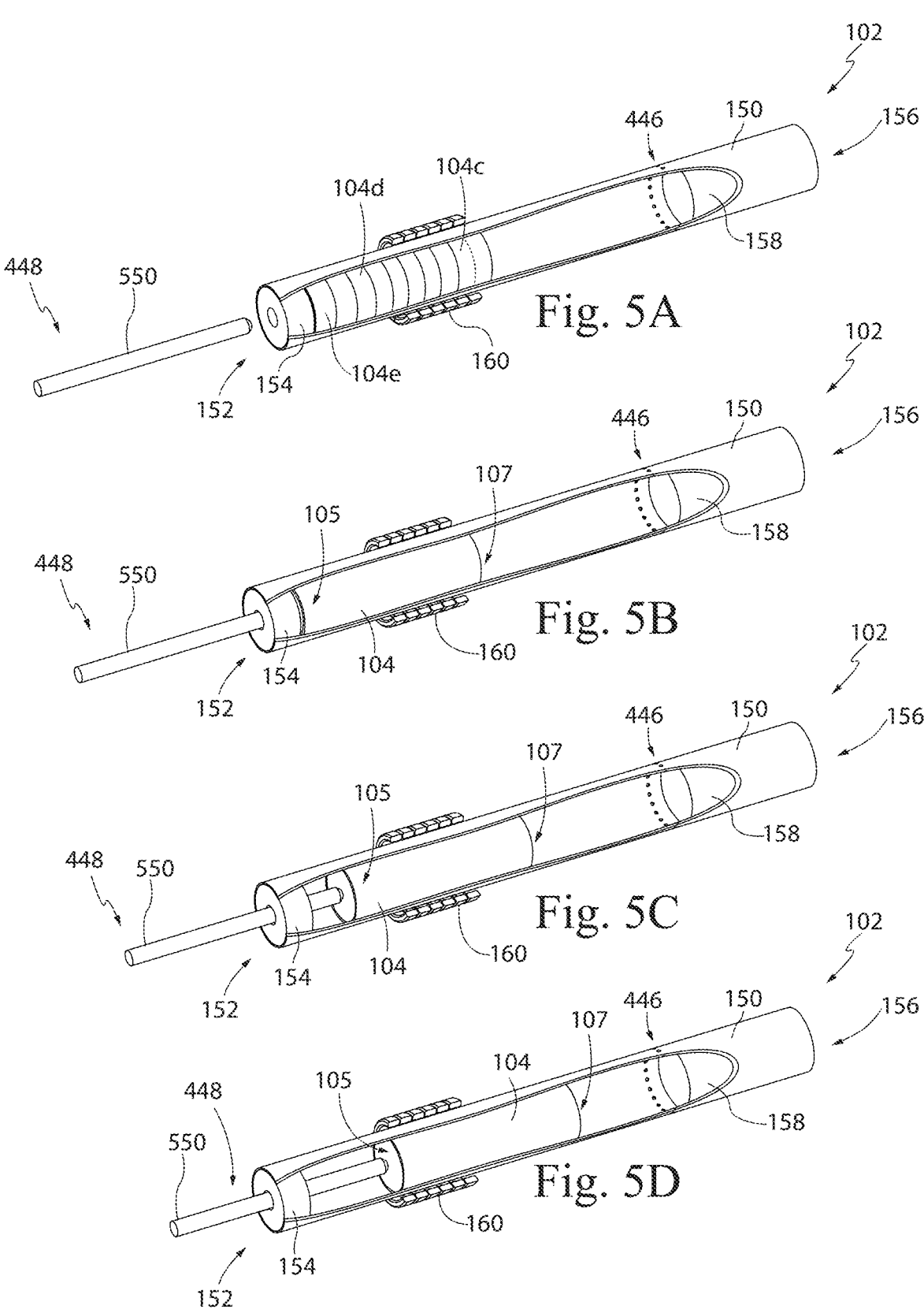
FIGS. 5A-5D show a series of perspective views of another embodiment of the present invention in which the consumable moves through the housing.
Figures 6A, 6B, 6C:
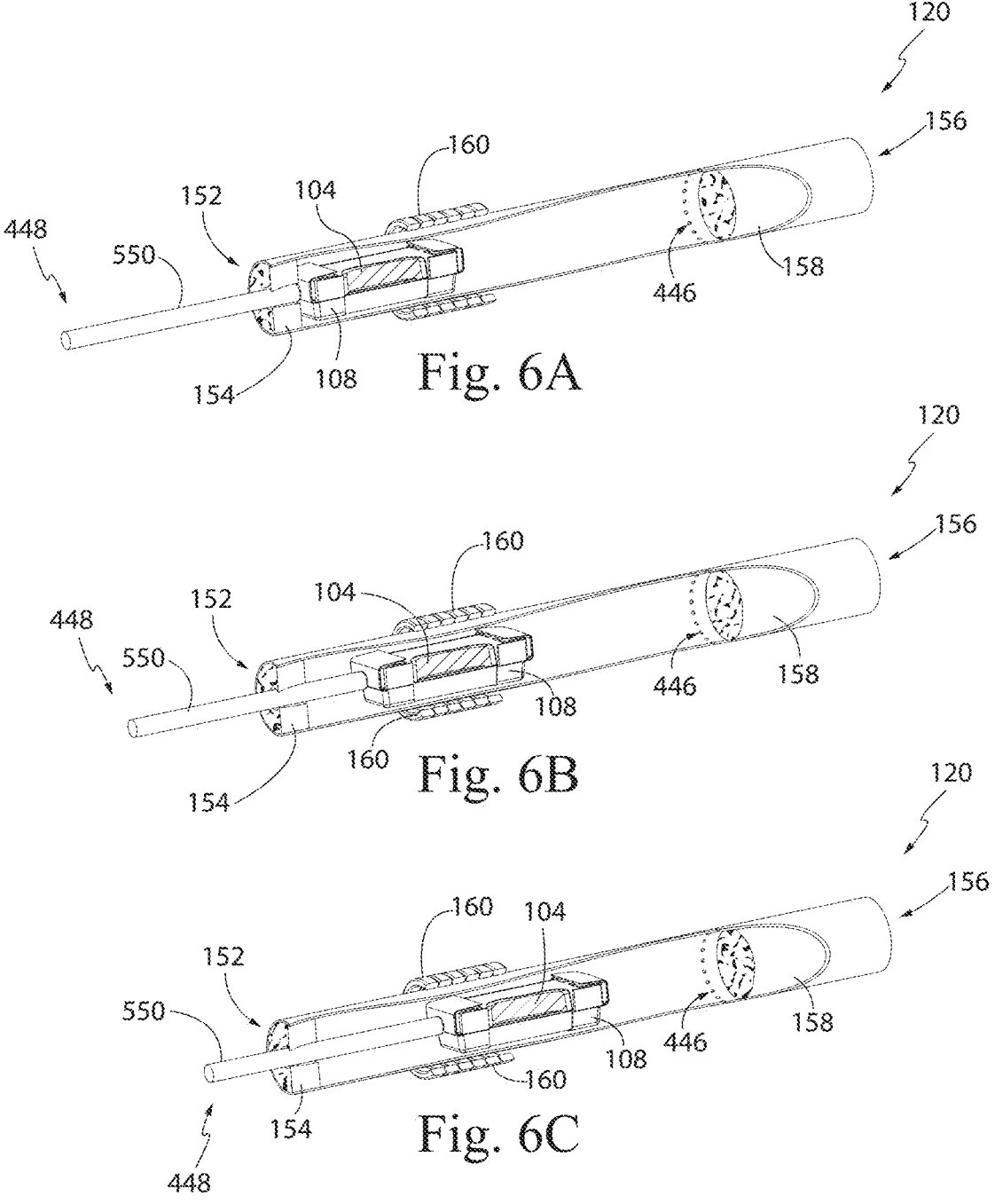
FIGS. 6A-6C show a series of perspective views of another embodiment of the present invention in which the consumable moves through the housing.
Figures 7A, 7B, 7C, 7D, 7E:
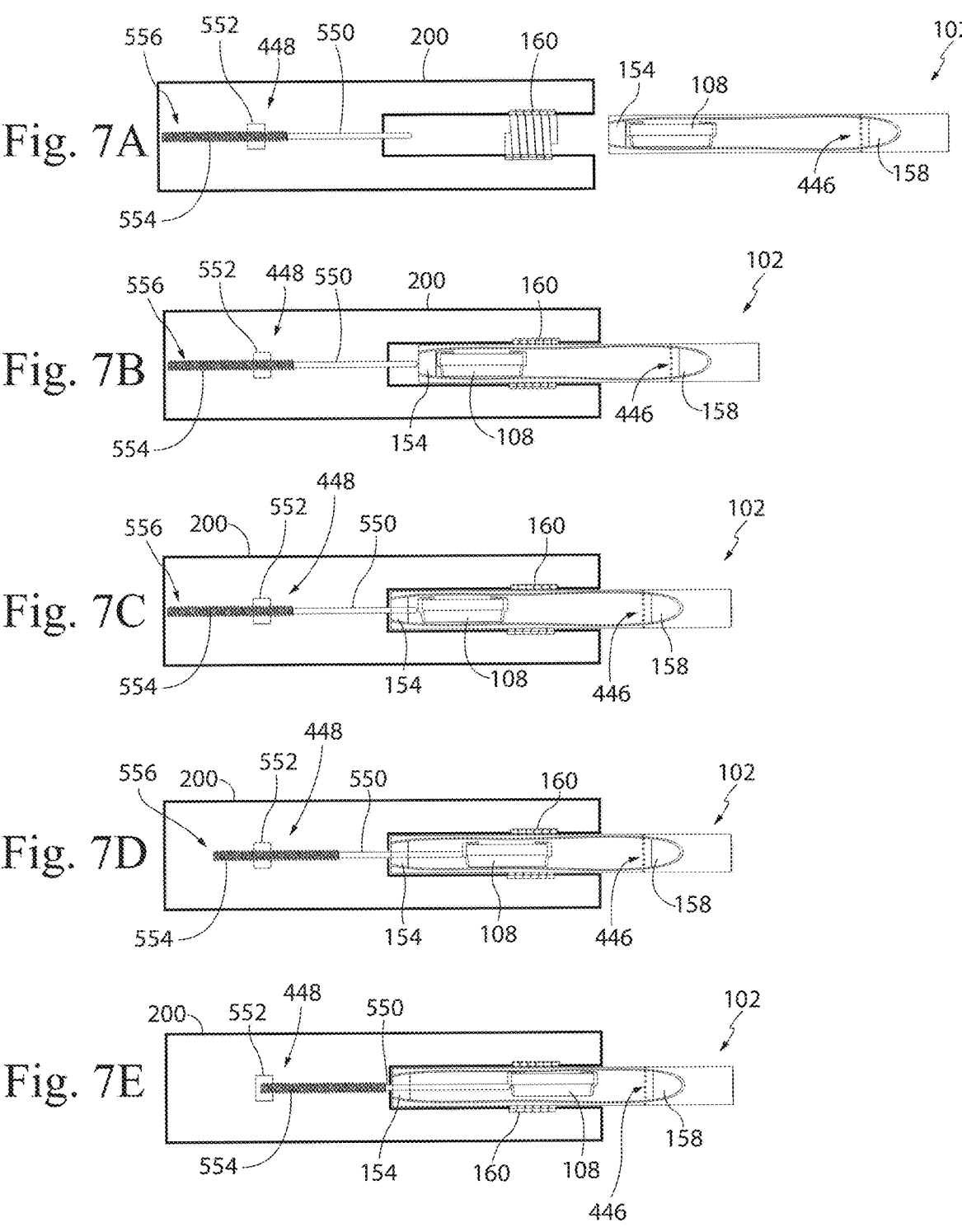
FIGS. 7A-7E show a series of perspective views of another embodiment of the present invention in which the consumable is inserted into a HNB device and the consumable moves through the housing.

In a preferred embodiment, to securely close the encasement 108 around the aerosol-producing substrate 104, the ends 124, 126 of the encasement 108 may have folds 130, 132 as shown in FIGS. 4A and 4B. Prior to folding, the two portions of the encasement 108a, 108b may be joined or sealed with conventional methods, such as adhesives, mechanical fasteners, crimping, RF welding, or any suitable method, to enclose the encasement 108. Likewise, after folding, the sealed/joined ends 124, 126 may be adhered to the outer surfaces of the encasement 108 as shown in FIG. 4A. Alternatively, the ends 124, 126 of the encasement 108 need not be sealed prior to folding, but instead held in folded pattern by adhesives, mechanical fasteners, crimping, RF welding, or any suitable method. In yet another alternative, the encasement 108 may simply be held in place by the folds themselves, without any sealing or joining.

Therefore, a method of manufacturing a consumable-containing package 102 for use in an aerosol-producing device 200 comprises combining a susceptor 106 with an aerosol-producing substrate 104 containing a consumable; covering the aerosol-producing substrate 104 with an encasement 108; folding the ends 124, 126 of the encasement 108 to enclose the aerosol-producing substrate 104; and placing the assembly into a housing 150.

In some embodiments, the encasement 108 may be eliminated altogether and the aerosol-producing substrate 104 is simply surrounded by the housing 150. In such an embodiment, the aerosol is released from the aerosol-producing substrate 104 directly into the channel between the aerosol-producing substrate 104 and the housing 150. Like the encasement embodiments, the exterior of the aerosol-producing substrate 104 does not reach combustion temperature due to the rapid inside-out inductive heating.

In embodiments where the encasement 108 is porous or absent, freshness of the consumable may be maintained by use of an airtight packaging, which may be filled with nitrogen or other inert gas to prevent oxidation. Such packaging could be used for large packages of consumable-containing packages 102, for example, with tobacco products where multiple consumable-containing packages 102 may be used each day. Alternatively, individual packaging may be used for consumable-containing packages 102 containing medicants, where the consumable is only used periodically.

The Housing

In a preferred embodiment, the encasement 108 is configured to be permeable to the aerosol to allow the aerosol to escape from the encasement 108. The aerosol-producing substrate 104 can be placed inside a housing 150 with or without the encasement 108 as described above. The housing 150 is preferably less permeable or impermeable to the aerosol. The housing 150 can mimic a cigarette. As such, the housing 150 can be an elongated structure having a first end 152 and a second end 156 opposite the first end 152. The housing 150 is inserted into the device 200 such that the inductive heating element 160 surrounds the housing 150. Current passing through the inductive heating element 160 can then heat up the susceptor 104 embedded in the aerosol-producing substrate 104 resulting in the aerosol-producing substrate being heated from the inside-out. When the aerosol-producing substrate 104 is heated by the susceptor 106, an aerosol is created containing the consumable. When the user draws on the housing 150, for example, by sucking on the second end 156, the aerosol escapes from the encasement 108, but not the housing 150. Due to the negative pressure created by the sucking at the second end 156, the aerosol is drawn towards the second end 156 through any space between the aerosol-producing substrate 104 and the housing 150. An opening in or around the first end 152 may be used to facilitate air flow around the outside of the aerosol-producing substrate 104 and towards the second end 156. Such opening may be equipped with a valve for one-way or restricted flow.

To allow for multiple dosages using a single consumable-containing package 102, a variety of strategies can be employed. For example, the inductive heating element 160 can wrap around a portion of the consumable-containing package 102. Only the portion of the consumable-containing package 102 that is surrounded by the heating element 160 is heated and the consumable released. The position of the inductive heating element 160 relative to the consumable-containing package 102 can then be modified to have the inductive heating element 160 surround a new portion of the consumable-containing package 102 that has not yet been sufficiently heated to release the consumable. To achieve this new position, either the inductive heating element 160 can be moved and the aerosol-producing substrate 104 kept stationary, or the aerosol-producing substrate 104 can be moved and the inductive heating element 160 kept stationary, or both the inductive heating element 160 and the aerosol-producing substrate 104 can be moved. In some embodiments, neither the inductive heating element 160 nor the aerosol-producing substrate 104 moves. Rather, the inductive heating element 160 can wrap around the full length of the aerosol-producing substrate 104 and specific segments of the inductive heating element 160 can be activated so as to only heat up specific portions 104c, 104d, 104e of the aerosol-producing substrate 104 at a given time.

As shown in FIGS. 5A-5D, 6A-6C, 7A-7E, and 8A-8B, in the preferred embodiment, the aerosol-producing substrate 104 is moved along the length of the housing 150 while the inductive heating element 160 remains stationary. By way of example only, the aerosol-producing device 200 can comprise a driver 448 that may be operatively connected or otherwise engaged with the aerosol-producing substrate 104 when the aerosol-producing substrate 104 is inserted into the aerosol-producing device 200. The driver 448 can be configured to advance the aerosol-producing substrate 104 through the housing 150. Advancement of the aerosol-producing substrate 104 through the housing 150 allows different portions of the aerosol-producing substrate 104c, 104d, 104e to be surrounded by the inductive heating element 160. Thus, in use, the aerosol-producing substrate 104 can be inserted into the housing 150 in a manner that allows the aerosol-producing substrate 104 to move from the end cap 154 to the mouthpiece 158 through the housing 150 such that portions 104, 104*d*, 104*e* of the aerosol-producing substrate 104 incrementally pass through the induction heating element 160 in series.

In the preferred embodiment, the driver 448 comprises a rod 550 and a rotatable collar 552 operatively connected to or otherwise engaged with the rod 550 to advance the rod 550. The collar 552 may be operated by a small motor operatively connected to the controller 166. The rod 550 can be inserted into the housing 150 through the end cap 154 until the rod 550 meets a first end 105 of the aerosol-producing substrate 104. In this position, a second end 107 of the aerosol-producing substrate 104*c* can be surrounded by the inductive heating element 160 (see, e.g., FIGS. 5A, 5B, 6A, and 7B). When the inductive heating element 160 is activated, the aerosol-producing substrate 104 is heated only at the portion where it is surrounded by the inductive heating element 160. When the driver 448 is activated, the collar 552 advances the rod 550 towards the second end 156 of the housing 150. This movement causes a new portion of the aerosol-producing substrate 104*d* (closer to the first end 105 of the aerosol-producing substrate 104) to be surrounded by the inductive heating element 160 (see, e.g., FIGS. 5C, 6B, and 7D). Activation of the inductive heating element 160 can now heat the new portion 104*d* of the aerosol-producing substrate 104 that was not heated previously, causing another dose of the consumable to be released as an aerosol for inhalation. The collar 552 can advance the aerosol-producing substrate again through the housing 150 placing yet another unheated portion 104*e* of the aerosol-producing substrate 104 (even closer to the first end 105 if not already at the first end 105) within the heating range of the inductive heating element 160 (see, e.g., FIGS. 5D, 6C, and 7E). This process can continue until the entire aerosol-producing substrate 104 has been heated and the consumable aerosol released.

In the preferred embodiment, the rod 550 can be a jack screw having threading 554 on a first end 556 as shown in FIGS. 7A-7E. The threading 554 on the first end 556 of the rod 550 can mate with a rotatable collar 552. Actuation of the driver 448 causes the collar 552 to rotate, which in turn causes the rod 550 to advance. Alternatively, the collar 552 could be fixed and the rod 550 could be engaged with a rotational mechanism to cause the rod 550 to advance when rotated. Other forms of drivers 448 for incrementally advancing the aerosol-producing substrate 104 along a linear path can be used, such as a driver 448 with a telescoping action, sliding action, rolling action, and the like, or any combination thereof. In addition, advancement of the aerosol-producing substrate may be by smooth, gradual movement, or more abrupt movement in a step-like manner. In an alternative embodiment, the aerosol-producing substrate 104 or some structure attached thereto could be threaded and engage with a threading on the housing 150, such that rotating the housing 150 or the aerosol-producing substrate 104 would advance the aerosol-producing substrate 104.

In some embodiments, in order to prevent the aerosol-producing substrate 104 from moving when not in use, and prior to the connection with the rod 550, the aerosol-producing substrate 104 can be bonded to the inside of the housing 150 with the first end 105 of the aerosol-producing substrate 104 adjacent to the rod 550. The bonding between the aerosol-producing substrate 104 can be tight enough that general movement and shaking of the housing 150 would not cause the aerosol-producing substrate 104 to move within the housing 150. Thus, movement associated with transportation and shipping of the housing would not be sufficient to cause the aerosol-producing substrate 104 from being released by the bond. In addition, the bonding between the aerosol-producing substrate 104 and the housing 150 can be strong enough to allow the rod 550 to be operatively connected to the aerosol-producing substrate 104. Advancement of the rod 550, however, is sufficient to break the bond between the aerosol-producing substrate 104 and the housing 150 allowing the aerosol-producing substrate 104 to advance through the housing 150. The new connection between the rod 550 and the aerosol-producing substrate 104 is sufficiently strong to prevent the aerosol-producing substrate 104 from moving around in the housing 150 during movement after the bond between the aerosol-producing substrate 104 and the housing 150 has been broken. Alternatively, if the bond is a temperature-sensitive material, the bond could be broken or weakened when the aerosol-producing substrate 104 is heated for the first time, prior to the rod 550 advancing.

To prevent unwanted movement of the aerosol-producing substrate 104 after the first use, however, such as when the device is tossed into a purse or onto a counter, the aerosol-producing substrate 104 may have a friction fit within the housing 150 that prevents movement except for that produced by the rod 550, or the aerosol-producing substrate 104 could be affixed or otherwise engaged to the rod 550 to prevent movement independent of the rod 550. Alternatively, the aerosol-producing substrate 104 may engage the housing or other structure with a threading or other structure that prevents unwanted movement of the aerosol-producing substrate 104.

Figures 8A, 8B:
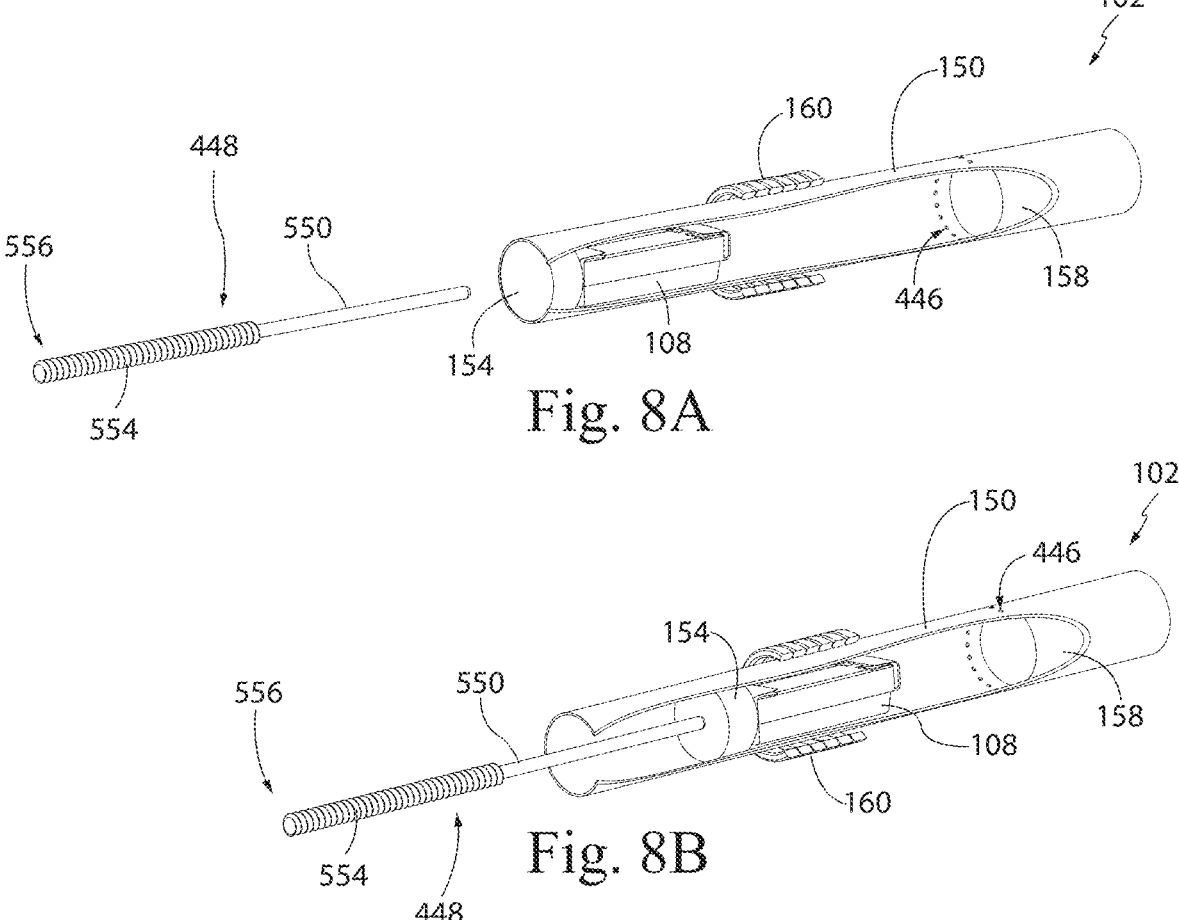
FIGS. 8A-8B show a series of perspective views of another embodiment of the present invention in which the consumable moves through the housing.

In some embodiments, the advancement of the rod 550 may only cause the aerosol-producing substrate 104 to advance through the housing 150. In some embodiments, the end cap 154 may also advance through the housing 150 as shown in FIGS. 8A-8B. As such, the aerosol-producing substrate 104 may be connected to the end cap 154, and the rod 500 may be connected to or otherwise engaged with the end cap 154. Therefore, advancement of the rod 500 causes the end cap 154 to advance through the housing 150 and the end cap 154 causes the aerosol-producing substrate 104 to advance through the housing 150.

Having established the general principles of the consumable-containing package 102, variations have also been contemplated that achieve the same objectives. For example, in some embodiments, the aerosol-producing substrate 104 may comprise two elongated sections 104*a*, 104*b*. The two elongated sections 104*a*, 104*b* of the aerosol-producing substrate 104 may be defined by a plane parallel to and cutting through the longitudinal axis A. Therefore, the two elongated sections 104*a*, 104*b* may be cuboid or half-cylinder sections that when mated together form a larger cuboid or full cylindrical aerosol-producing substrate 104.

In some embodiments, the encasement 108 may be made of porous material. For example, the encasement 108 may be a porous paper wrap, or other similar material. As such, the pores would function as the openings 120 by allowing the aerosol from the aerosol-producing substrate 104 to escape when heated. Furthermore, because the aerosol-producing substrate 104 may be compressed so as to eliminate the oxygen, combustion is still unlikely at the working temperatures and for the short duration of time the aerosol-producing substrate 104 is exposed to the high heat. Even though the exterior of the encasement 108 is exposed to oxygen along the channel between the encasement 108 and the housing 150, the inductive heating rapidly heats the consumable from the inside-out, so the exterior of the encasement 108 never reaches combustion temperature.

In embodiments in which the encasement 108 is a porous material, the encasement 108 allows the aerosol to pass through the pores of the encasement 108 and exit the encasement 108 laterally or radially outwardly. This allows the aerosol to enter the channel created between the housing 150 and the encasement 108.

In a preferred embodiment, the aerosol-producing substrate 104 is cuboid shaped and the housing 150 is cylindrical, which creates four channels between the aerosol-producing substrate 104 and the housing 108, between the generally planar faces of the cuboid and the cylinder wall (i.e. above, below, and bilaterally along the sides of the aerosol-producing substrate 104). Although cuboid is a preferred shape of the aerosol-producing substrate 104 and cylindrical is the preferred shape of the housing 108, any shape may be used for either of them.

In some embodiments, the encasement 108 may be thicker and have sufficient porosity to allow the aerosol to travel through the pores longitudinally along the axis A through the length of the encasement 108. In such an embodiment, a designated channel may not be needed between the housing 150 and the encasement 108 as the aerosol can travel through the encasement 108. Such porous materials may include cigarette paper, cellulose or other filter media, or any suitable material for the purpose.

The encasement 108 containing the aerosol-producing substrate 104 can then be inserted into the housing 150 to form the consumable-containing package 102. When the susceptor 106 is heated, the consumable aerosolizes and escapes into the porous encasement 108. When the user draws on the mouthpiece 158, the negative pressure created inside the housing 150 causes and airflow in the direction of the mouthpiece 158, and the aerosolized consumable travels through the pores of the encasement 108 towards the mouthpiece 158 where the consumable can be inhaled by the user.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A device for generating aerosol, comprising:
   (a) an aerosol-producing substrate;
   (b) a susceptor embedded within the aerosol-producing substrate;
   (c) a housing to contain the aerosol-producing substrate; and
   (d) an aerosol-producing device configured to receive the housing, the aerosol-producing device comprising
      (i) a driver operatively connected with the aerosol-producing substrate to drive the aerosol-producing substrate through the housing; and
      (ii) an induction heating element surrounding at least a portion of the housing, wherein the driver is configured to advance the aerosol-producing substrate through the housing such that portions of the aerosol-producing substrate pass through the induction heating element in series, wherein the driver comprises a rod operatively connected with the aerosol-producing substrate.

2. The device of claim 1, wherein the rod is threaded at a first end to advance the aerosol-producing substrate gradually.

3. The device of claim 1, wherein the aerosol-producing substrate comprises an elongated member.

4. The device of claim 1, wherein the elongated member has a polygonal transverse cross-section.

5. The device of claim 4, wherein the aerosol-producing substrate is at least partially within an encasement.

6. A method for aerosolizing a consumable contained throughout an aerosol-producing substrate by an aerosol-producing device, the method comprising:
   (a) inserting an aerosol-producing substrate with an embedded susceptor into a housing;
   (b) inserting the housing into an aerosol-producing device that comprises an induction heating element;
   (c) surrounding a first portion of the aerosol-producing substrate and the housing with the induction heating element;
   (d) heating the susceptor by activating the induction heating element, whereby the consumable located in the first portion of the aerosol-producing substrate is aerosolized;
   (e) advancing the aerosol-producing substrate through the housing so that a second portion of the aerosol-producing substrate is surrounded by the induction heating element; and
   (f) activating the induction heating element, whereby the consumable located in the second portion of the aerosol-producing substrate is aerosolized, wherein advancing the aerosol-producing substrate comprises a driver operatively engaging with the aerosol-producing substrate, and wherein the housing comprises an end cap at a first end and a mouthpiece at a second end opposite the first end, and wherein the driver comprises a rod operatively connected with the aerosol-producing device via the end cap.

7. The method of claim 6, wherein the driver advances the end cap.

8. The method of claim 6, wherein the driver advances the aerosol-producing substrate without advancing the end cap.

9. The method of claim 6, wherein the aerosol-producing substrate comprises an elongated member with a polygonal transverse cross-section.

10. A method for manufacturing a device for generating aerosol, comprising:
   (a) providing an aerosol-producing substrate containing a consumable;
   (b) embedding a susceptor inside the aerosol-producing substrate;
   (c) placing the aerosol-producing substrate inside a housing; and
   (d) providing an aerosol-producing device, the aerosol-producing device comprising:
      (i) an induction heating element configured to surround at least a portion of the housing; and
      (ii) a driver operatively connected with the consumable-producing substrate to advance the aerosol-producing substrate through the induction heating element while the housing is stationary, further comprising providing an end cap positioned at a first end of the housing, and a mouthpiece at a second end of the housing.

11. The method of claim 10, further comprising engaging a rod from the driver with the aerosol-producing substrate via the end cap.

12. The method of claim 11, further comprising advancing the aerosol-producing substrate through the induction heating element by advancing the end cap.

13. The method of claim 11, further comprising advancing the aerosol-producing substrate without advancing the end cap.

14. The method of claim 11, wherein the aerosol-producing substrate comprises an elongated member with a polygonal transverse cross-section.

* * * * *